United States Patent
Liang et al.

(10) Patent No.: US 12,424,314 B2
(45) Date of Patent: Sep. 23, 2025

(54) COMMUNICATION SYSTEM AND METHOD FOR RESPIRATORY PROTECTION DEVICE, AND RESPIRATORY PROTECTION SYSTEM

(71) Applicant: CHANGZHOU SHINE SCIENCE & TECHNOLOGY CO. LTD., Changzhou (CN)

(72) Inventors: Dong Liang, Changzhou (CN); Liang Chen, Changzhou (CN)

(73) Assignee: CHANGZHOU SHINE SCIENCE & TECHNOLOGY CO. LTD., Changzhou (CN)

( * ) Notice: Subject to any disclaimer, the term of this patent is extended or adjusted under 35 U.S.C. 154(b) by 0 days.

(21) Appl. No.: 19/027,473

(22) Filed: Jan. 17, 2025

(65) Prior Publication Data

US 2025/0273328 A1    Aug. 28, 2025

Related U.S. Application Data

(63) Continuation of application No. PCT/CN2024/139078, filed on Dec. 13, 2024.

(30) Foreign Application Priority Data

Feb. 23, 2024  (CN) .......... 202410202269.1

(51) Int. Cl.
*G16H 40/60*  (2018.01)
*H04W 64/00*  (2009.01)
*H04W 76/14*  (2018.01)

(52) U.S. Cl.
CPC .......... *G16H 40/60* (2018.01); *H04W 64/003* (2013.01); *H04W 76/14* (2018.02)

(58) Field of Classification Search
CPC ..... G16H 40/60; H04W 64/003; H04W 76/14
See application file for complete search history.

(56) References Cited

FOREIGN PATENT DOCUMENTS

| CN | 103347307 A |   | 10/2013 |
|----|-------------|---|---------|
| CN | 113613549 A | * | 11/2021 |
| CN | 117114454 A |   | 11/2023 |

OTHER PUBLICATIONS

Ming et al, English translation of CN113613549, Medical Device Pairing System and Method, pp. 1-21 (Year: 2025).*

* cited by examiner

*Primary Examiner* — Brian A Zimmerman
*Assistant Examiner* — Cal J Eustaquio
(74) *Attorney, Agent, or Firm* — Nitin Kaushik

(57) ABSTRACT

The invention belongs to the technical field of respiratory protection, and particularly relates to a communication system and method for a respiratory protection device, and a respiratory protection system. The system includes pairing transmission modules, each with a first and second pairing unit, and a main control module containing a communication unit, control unit, and storage unit. The communication unit links the transmission modules for data transmission, while the control unit processes identity and pairing information. This system enables effective communication between the respiratory protection device and the main control module. By establishing a database of multiple devices, the control module facilitates data analysis, mining, and visualization, uncovering patterns and supporting decision-making. The unified platform or system may also integrate with other systems to achieve automated decision control and monitoring management, enhancing the intelligence level of the system.

7 Claims, 3 Drawing Sheets

COMMUNICATION SYSTEM AND METHOD FOR RESPIRATORY PROTECTION DEVICE, AND RESPIRATORY PROTECTION SYSTEM

CROSS-REFERENCE TO RELATED APPLICATIONS

The application claims priority to Chinese patent application No. 2024102022691, filed on Feb. 23, 2024, the entire contents of which are incorporated herein by reference.

TECHNICAL FIELD

The invention belongs to the technical field of respiratory protection, and particularly relates to a communication system and method for a respiratory protection device, and a respiratory protection system.

BACKGROUND

The electric respiratory device generally includes a main unit that can be worn around the waist, a filter component detachably mounted on the main unit, a face shield, a connecting tube located between the main unit and the face shield, a battery pack, and other components.

To ensure the best performance for users, it is essential to guarantee the installation stability of the aforementioned components. For example, the filter component, such as filter cartridge and filter canister, must be properly installed to ensure effective filtration. Additionally, the installation stability of the connecting tube must be ensured to facilitate smooth airflow between the main unit and the face shield. Further, it is necessary to ensure that some components operate within their effective usage time, which is particularly critical for the filter component. For instance, for users using respiratory protection devices in toxic environments, the filter canister can only provide respiratory protection for a limited time. If used beyond the specified duration, the filter canister is likely to be compromised by toxic gases, posing a risk to user safety. Therefore, it is essential to record the usage time of each filter canister, so as to alert users when it is approaching its breakthrough time and needs to be replaced to avoid safety hazards. Moreover, based on noise regulations, airflow control must be implemented accordingly for different filter components. For example, the resistance of the filter canister is greater than that of the filter cartridge, and the filter canister can only meet the relevant noise requirements when operating at the first speed. Thus, the airflow setting for the filter canister should be reduced, while the standard filter cartridge may allow for airflow settings at the second or third speeds.

To address the aforementioned needs, there are currently effective technological means available, such as using positioning detectors to detect whether the filter components are properly installed, as well as accurately identifying the types and usage durations of the filter components. However, the current detection and identification results only correspond to the use of individual respiratory protection devices, meaning users can only make manual judgments and operations regarding the usage status of the respiratory protection device based on the corresponding data.

With advancements in product technology, effective analysis and decision-making control at the big data level has become one of the directions for product design and control. This requires integrating the aforementioned data into a unified platform or system. Therefore, a dedicated system capable of achieving data communication for respiratory protection devices has become a technical requirement in this field.

SUMMARY

The invention provides a communication system and method for a respiratory protection device, and a respiratory protection system, which can effectively solve the problems in the background art.

To achieve the above objective, the invention adopts the following technical scheme.

A communication system for a respiratory protection device comprises:
 pairing transmission modules, each comprising a first pairing unit and a second pairing unit which are paired and connected within a specified location area and are respectively installed on different components of the respiratory protection device; and
 a main control module connected with the plurality of pairing transmission modules and comprising a communication unit, a control unit and a storage unit; wherein
 the communication unit is in communication connection with the pairing transmission modules for information transmission;
 the control unit collects and processes identity information of the first pairing unit and/or the second pairing unit and pairing information of the first pairing unit and the second pairing unit, the identity information at least comprising component information of the corresponding respiratory protection device; and
 the storage unit stores collection and processing results of the identity information and the pairing information.

Further, the communication system for a respiratory protection device further comprises a positioning module installed at a specified location of the respiratory protection device;
 the communication unit is in communication connection with the positioning module;
 the control unit collects and processes positioning information of the positioning module; and
 the storage unit stores collection and/or processing results of the positioning information.

Further, the collection and processing of the identity information by the control unit comprises:
 continuously assessing whether a new pairing transmission module is successfully paired until the assessment result is yes, and collecting the identity information of the first pairing unit and/or the second pairing unit in the pairing transmission module; and
 endowing the identity information with:
 a unique identifier part which records unique identifier of the specified components on the respiratory protection device where the first pairing unit and/or the second pairing unit are installed; and
 a dynamic identifier part which records real-time setting parameters of the specified components.

Further, the storage unit stores the unique identifier part only once through a first storage area, and stores the dynamic identifier part corresponding to the unique identifier part through a second storage area.

Further, establishing a correspondence between the first storage area and the second storage area comprises:
 establishing a virtual file system in the first storage area, and mapping each unique identifier to a unique file path or file name; and storing dynamic data of the real-time setting parameters in the second storage area in the form of files, paths or file names of each file corresponding to the unique identifiers.

Further, the main control module also comprises a data processing unit which processes and analyzes the data stored in the storage unit and predicts a usage status of the respiratory protection device according to analysis results.

Further, the data processing unit comprises:
a data processor for processing the data obtained from the storage unit, the processing at least comprising data cleaning, conversion, normalization and feature engineering;
data analysis algorithms which deeply analyze and mine the processed data to find trends and correlations in the data and obtain analysis results; and
a prediction model which is established according to the analysis results and used for predicting a future usage status of the respiratory protection device.

Further, the prediction model is an LSTM model, comprising:
an input layer for receiving the analysis results;
an LSTM layer for learning the long-term dependence of time series data in the analysis results and generating an internal representation;
an output layer for receiving the internal representation from the LSMT layer and generating final prediction results; and
a sliding window which divides the time series data from the analysis results into different windows and allows for movement on a time axis in a sliding manner to generate a series of subsequence data and input the same into the LSTM layer.

A communication method for a respiratory protection device, which adopts the communication system for a respiratory protection device as described above, comprises:
collecting pairing information of two components installed on the respiratory protection device and requiring relative installation, and collecting component information of at least one of the components;
transmitting the pairing information and the component information through communication connection;
processing the transmitted pairing information and component information; and
storing different processing results of the pairing information and component information in a centralized manner.

A respiratory protection system comprises a plurality of respiratory protection devices and the communication system for a respiratory protection device as described above;
the communication system comprises a plurality of pairing transmission modules which are respectively installed on two different components requiring relative installation on the plurality of respiratory protection devices;
the communication system collects, processes and stores the identity information and pairing information of different respiratory protection devices in a centralized manner through the main control module and the plurality of pairing transmission modules; and
the main control module is connected with a fan of the respiratory protection device, at least controls the supplied airflow of the fan according to processing results, and monitors a usage status of the specified component.

Through the technical scheme of the invention, the following technical effects can be achieved.

The communication system enables effective communication between the respiratory protection device and the main control module. By establishing a database of multiple respiratory protection devices through the main control module, data can be analyzed, mined, and visualized to uncover relationships and patterns among the data, thereby providing support for decision-making. Based on the results of data analysis, corresponding decision-making and control strategies can be developed, such as creating device maintenance plans, optimizing device design, and improving production efficiency. The unified platform or system may also integrate with other systems to achieve automated decision control and monitoring management, enhancing the intelligence level of the system.

BRIEF DESCRIPTION OF DRAWINGS

In order to more clearly explain the embodiments of the invention or the technical scheme in the prior art, the following will briefly introduce the drawings needed in the description of the embodiments or the prior art. Obviously, the drawings in the following description are only some embodiments of the invention. For those of ordinary skill in the art, other drawings can be obtained according to the provided drawings without paying creative labor.

DETAILED DESCRIPTION OF THE EMBODIMENTS

The technical schemes in the embodiments of the present invention are clearly and completely described in the following with reference to the drawings in the embodiments of the present invention. It is obvious that the described embodiments are only some of the embodiments of the present invention and are not all the embodiments thereof.

Unless otherwise defined, all technical terms and scientific terms used herein have the same meanings as commonly understood by those skilled in the technical field of the invention. The terms used in the specification of the invention are only for the purpose of describing specific embodiments. are not intended to limit the invention. As used herein, the term "and/or" includes any and all combinations of one or more related listed items.

Embodiment I

Figure 1:
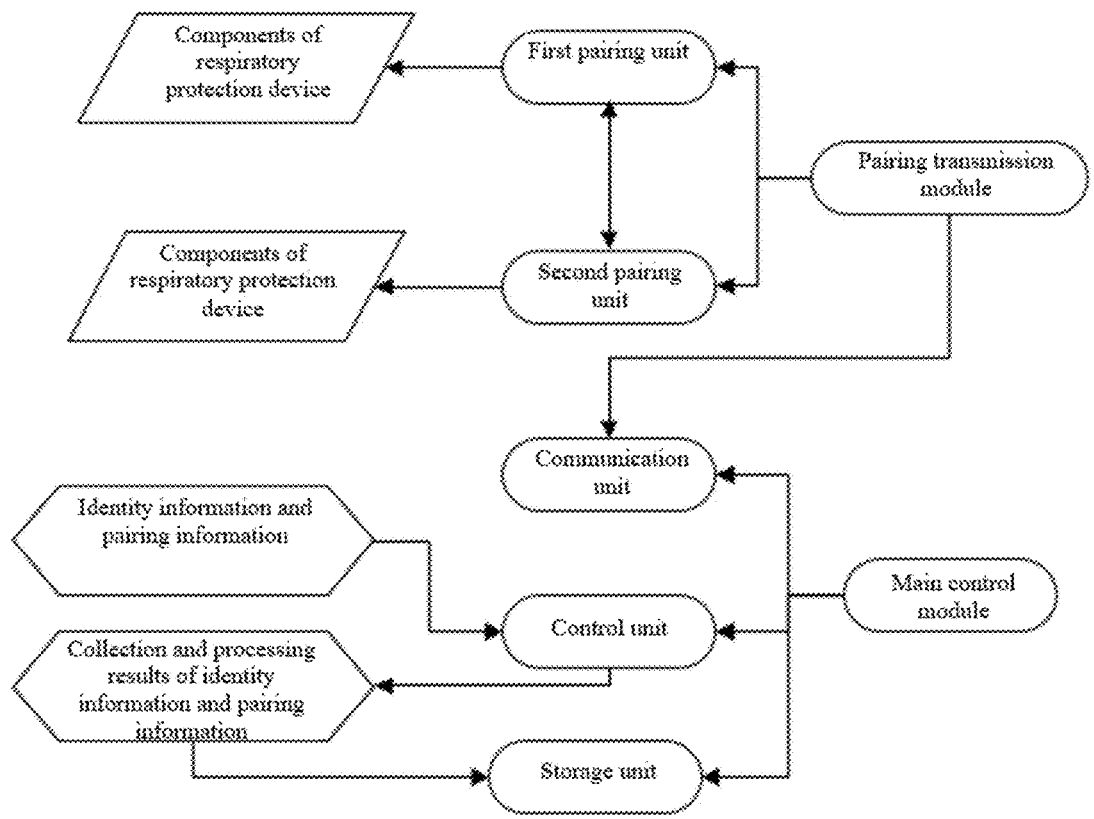
FIG. 1 is a frame diagram of a communication system for a respiratory protection device.

Referring to FIG. 1, a communication system for a respiratory protection device comprises:
pairing transmission modules, each comprising a first pairing unit and a second pairing unit which are paired and connected within a specified location area and are respectively installed on different components of the respiratory protection device; and
a main control module connected with the plurality of pairing transmission modules and comprising a communication unit, a control unit and a storage unit; wherein
the communication unit is in communication connection with the pairing transmission modules for information transmission;
the control unit collects and processes identity information of the first pairing unit and/or the second pairing unit and pairing information of the first pairing unit and the second pairing unit, the identity information at least comprising component information of the corresponding respiratory protection device; and the storage unit stores collection and processing results of the identity information and the pairing information.

In this embodiment, the arrangement of the first pairing unit and the second pairing unit within the pairing transmission module effectively addresses the assembly assessment of various components in the respiratory protection device. During use, the first pairing unit and the second pairing unit are installed on two components to be installed relative to each other. This allows for the determination of whether the installation of the two components is in place by establishing or breaking the pairing connection. For instance, in the application of the communication system, the first pairing unit of one pairing transmission module can be installed on a filter component, and the second pairing unit on a housing. The successful pairing of the first pairing unit and the second pairing unit can confirm that the filter component is properly installed relative to the housing. Additionally, in another example, the first pairing units of a set of pairing transmission modules are installed at one end of a connecting tube, and the second pairing units on a main unit or face shield. The successful pairing of the first pairing units and the second pairing units indicates that the connecting tube is properly installed relative to the main unit or face shield.

The main control module is connected to the plurality of pairing transmission modules, enabling simultaneous installation accuracy assessment of multiple sets of components on multiple respiratory protection devices, while also serving as a platform for data storage and processing. The tasks performed by the main control module include the collection and processing of identity information of the first pairing unit and/or the second pairing unit. This includes scenarios where only the identity information of the first pairing unit is collected and processed, only the identity information of the second pairing unit is collected and processed, or the identity information of both the first pairing unit and the second pairing unit is collected and processed simultaneously. During the implementation process, the purpose of identity information recognition includes at least determining the information of the components where the first pairing unit and the second pairing unit are installed based on the identity information. For example, if the first pairing unit is installed on the filter component, the identity information can reflect the model, usage duration, usage status, and more of the filter component.

The storage unit stores the collection time of the information, raw data, processing results, and other related information for future use.

The communication system enables effective communication between the respiratory protection device and the main control module. By establishing a database of multiple respiratory protection devices through the main control module, data can be analyzed, mined, and visualized to uncover relationships and patterns among the data, thereby providing support for decision-making. For example, the service life of different types of filter components and the stability of devices under different pairing conditions can be analyzed. Based on the results of data analysis, corresponding decision-making and control strategies can be developed, such as creating device maintenance plans, optimizing device design, and improving production efficiency. The unified platform or system may also integrate with other systems to achieve automated decision control and monitoring management, enhancing the intelligence level of the system.

During the implementation process, pairing signals can be transmitted using one or more of the following methods: Bluetooth, Zigbee, Wi-Fi, ultra-wideband (UWB), NFC (13.56 MHz, 433 MHZ, 860 MHz-960 MHz), and 2.4G devices. For the communication connection between the communication unit and the pairing transmission module, one or more of the following technologies can be employed: GPRS/CDMA wireless communication, data radio communication, spread spectrum microwave communication, wireless bridges, satellite communication, and shortwave communication. When selecting communication technologies, factors such as security, cost, energy consumption, and compatibility with the hardware and software of the devices must be considered. After comprehensively evaluating these factors, the most suitable communication technology can be chosen based on actual needs to ensure the stability and reliability of the communication.

As a preferred option of the above embodiment, the communication system for a respiratory protection device further comprises a positioning module installed at a specified location of the respiratory protection device;

the communication unit is in communication connection with the positioning module;

the control unit collects and processes positioning information of the positioning module; and the storage unit stores collection and/or processing results of the positioning information.

The location information collected by the positioning module enables effective management and maintenance of the respiratory protection device. Users can easily track the location history of the device, understand its usage, and monitor location changes, aiding in the development of more effective maintenance plans and management strategies. The positioning module provides precise location information, which is particularly useful in complex environments or scenarios requiring quick localization. For instance, in emergencies, it allows for accurate identification of the location of the device and users, thereby accelerating rescue efforts. Additionally, location data can be used to analyze usage patterns and behaviors of the device. By examining the usage of the device in different locations, potential areas for improvement and optimization can be identified, enhancing the performance and efficiency of the device.

For communication system products, the positioning module can be integrated with the first pairing unit and/or the second pairing unit in the pairing transmission module and installed as a whole. This reduces installation complexity, which is beneficial for the application of the communication system.

Figure 2:
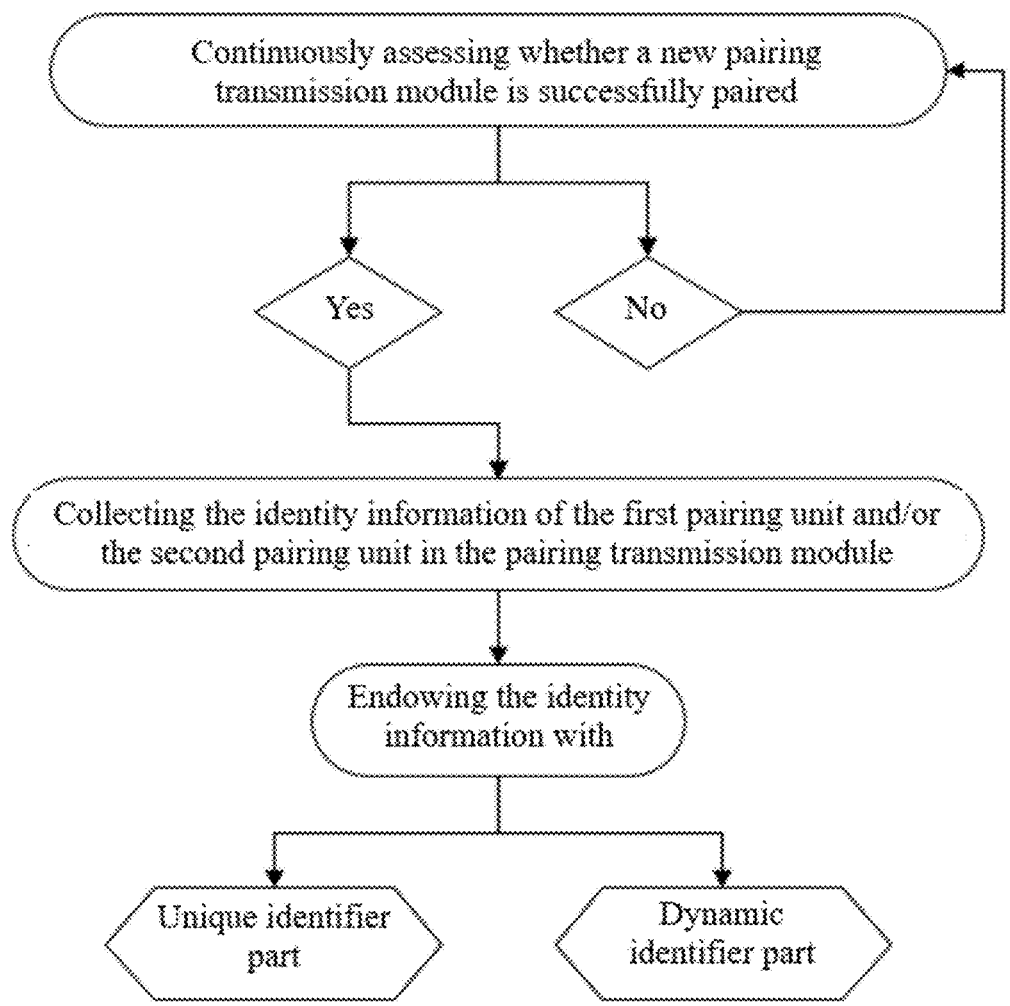
FIG. 2 is a flowchart of the collection and processing of identity information by a control unit.

As a preferred option of the above embodiment, as shown in FIG. 2, the collection and processing of the identity information by the control unit comprises:

continuously assessing whether a new pairing transmission module is successfully paired until the assessment result is yes, and collecting the identity information of the first pairing unit and/or the second pairing unit in the pairing transmission module; and endowing the identity information with:

a unique identifier part which records unique identifier of the specified components on the respiratory protection device where the first pairing unit and/or the second pairing unit are installed; and a dynamic identifier part which records real-time setting parameters of the specified components.

In the above embodiment, the system can promptly identify and record new pairing situations. In addition to the initial installation, this process is particularly critical during the subsequent replacement of the filter component, as it aids in the accurate recognition of new filter components. This helps ensure that the real-time status of each component in the device is accurately monitored and recorded, thereby enhancing the real-time performance and reliability of the system.

During the implementation process, identity information collection is not required for certain components of the respiratory protection device. For instance, when installing the filter component relative to the housing of the respiratory protection device, it is necessary to identify the relative installation positions through the first pairing unit connected to the housing and the second pairing unit connected to the filter component. As for identity information, it is sufficient to identify component information of the filter component only through the second pairing unit, without the need to identify component information of the housing through the first pairing unit. Specifically, it is necessary to collect component information for components critical to lifespan, such as battery packs, main units, and filter components. For components like face shields, connecting tubes, and housings, specific selections can be made based on actual needs.

By endowing the identity information with the unique identifier part, the system can record the unique identifiers of the specified components corresponding to the first pairing unit and/or the second pairing unit in the pairing transmission module. This design ensures that each component has distinct identity information, avoiding information confusion and misidentification, thus enhancing the accuracy and credibility of the data. The dynamic identifier part records the real-time setting parameters of the specified components, meaning the system can record the current status and parameter information of each component in the device in real time. This helps users stay informed about the usage status and performance parameters of the device, facilitating timely adjustment and optimization for improved operational efficiency and performance. By recording the unique identifiers and dynamic parameters of each specified component, the system can achieve personalized management and optimization for each component. For instance, tailored maintenance plans and optimization strategies can be developed for different components, thereby enhancing the lifespan and performance of the device.

By continuously collecting and processing the identity information, the system can accumulate a vast amount of data for data analysis and decision-making support. By analyzing the pairing situations and dynamic parameter changes of the components in the device, potential problems and areas for improvement can be identified, guiding future device design and management strategies.

From the perspective of optimizing data storage, as a preferred option of the above embodiment, the storage unit stores the unique identifier part only once through a first storage area, and stores the dynamic identifier part corresponding to the unique identifier part through a second storage area.

In the aforementioned optimization scheme, by storing the unique identifier part only once, redundant storage of the same identity information is avoided, effectively saving storage space. This is particularly important for the storage and management of large amounts of data, helping to reduce system costs and improve storage efficiency. Establishing dedicated storage areas for the dynamic identifier part and the unique identifier part ensures consistency and correlation between the data. This design allows related data to be stored and managed in groups, enhancing data reliability and management efficiency. By creating a dedicated storage area for the dynamic identifier part, related data can be organized and stored together, facilitating subsequent data retrieval and processing. This helps to improve data access speed and processing efficiency, thereby enhancing the performance and responsiveness of the system. By optimizing the design of the storage unit, the phenomenon of redundant storage of identical data is prevented, decreasing the likelihood of data redundancy. This contributes to maintaining data consistency and integrity while minimizing the complexity and risks of data management.

As a preferred option of the above embodiment, establishing a correspondence between the first storage area and the second storage area comprises:
  establishing a virtual file system in the first storage area, and mapping each unique identifier to a unique file path or file name; and
  storing dynamic data of the real-time setting parameters in the second storage area in the form of files, paths or file names of each file corresponding to the unique identifiers.

During the implementation process, it is essential to ensure that each unique identifier in the first storage area has a corresponding dynamic data file, and that the naming conventions for paths or file names clearly relate to the unique identifiers. This way, when dynamic data corresponding to a specific unique identifier is needed, one can simply use the unique identifier to construct the file path or name, allowing accurate retrieval of the corresponding dynamic data file.

In the first storage area, a virtual file system is established where each unique identifier is mapped to a unique file path or name. For example, if the unique identifier is ID_001, it may be mapped to the path/unique_id/ID_001 or the name ID_001.txt. In the second storage area, the corresponding dynamic data file may be stored at the path/dynamic_data/ID_001_data.txt or the name ID_001_data.txt.

The collection and processing of the pairing information by the control unit generally includes the following aspects:
  when pairing is successful, the control unit records the time of the successful pairing, the unique identifier of the device, and the structural information of the successful pairing, such as the pairing of the filter component and the housing. The information may assist in subsequent data analysis and device management;
  the control unit verifies and parses the pairing information to ensure the accuracy and completeness of the information, which at least involves validating the structural information of the successful pairing to check if the structure of the successful pairing meets the expected assembly conditions of the device;
  additionally, the control unit often conducts further processing of the pairing information to meet specific needs; for instance, the control unit may analyze the assembly status of the device based on the structural information of the successful pairing, monitoring the assembly accuracy and stability of the device; when detecting anomalies or inconsistencies in the pairing information, the control unit may trigger alarms or an exception handling mechanism; for example, if the pairing information indicates a mismatch or irrationality in the pairing structure, an alarm may need to be triggered, followed by further inspection and processing.

As a preferred option of the above embodiment, the main control module also comprises a data processing unit which processes and analyzes the data stored in the storage unit and predicts a usage status of the respiratory protection device according to analysis.

In this preferred scheme, since the data processing unit directly retrieves data from the storage unit, it ensures that the processed data is consistent with the stored data, thereby avoiding issues of data inconsistency or conflict. The data stored in the storage unit is updated in real time, allowing the data processing unit to access the latest data instantly for real-time processing and analysis. Further, the data in the storage unit is stored only after verification and confirmation, ensuring the accuracy and reliability of the data. The data processing unit performs processing and analysis based on the accurate data, leading to precise prediction results.

During the implementation process, predicting the usage status of the respiratory protection device allows for timely detection of potential issues or signs of failure, enabling preventive maintenance measures to be taken. This helps avoid unexpected breakdowns or damage, thereby enhancing the reliability and continuity of the device. The prediction results may also facilitate reasonable planning and optimization of resource utilization, including manpower, materials, and devices, leading to improved resource efficiency and reduced production costs. Additionally, appropriate measures may be taken based on the prediction results to minimize excessive use or improper operation of the device, extending its lifespan and lowering maintenance and replacement costs. Timely detection of safety hazards or risk factors related to the device can lead to the implementation of necessary safety measures, ensuring the safety of operators and the production environment.

Figure 3:
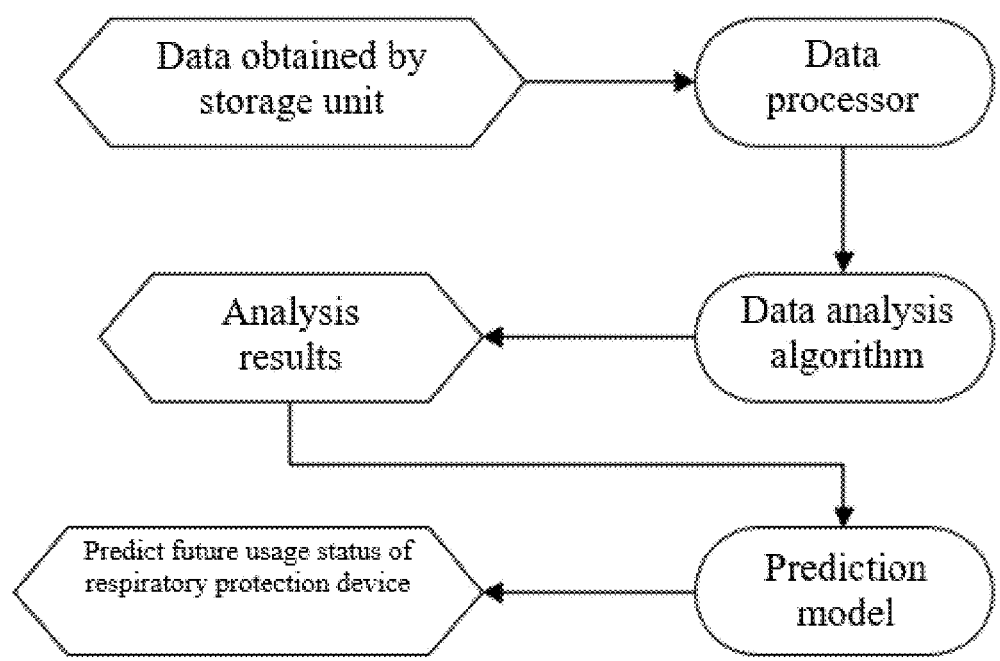
FIG. 3 is a frame diagram of a data processing unit.

As a preferred option of the above embodiment, as shown in FIG. 3, the data processing unit comprises:
- a data processor for processing the data obtained from the storage unit, the processing at least comprising data cleaning, conversion, normalization and feature engineering;
- here, data cleaning is used to detect and correct errors, missing values, or abnormal values in the data, ensuring the quality and consistency of the data; data conversion involves converting the data from its raw format into a format suitable for analysis and modeling, such as encoding data into numerical types or converting categorical variables into numerical ones; data normalization adjusts the scale and range of the data to ensure that the weights of different features are relatively consistent, preventing certain features from disproportionately influencing the model; and feature engineering refers to enhancing the representational capacity of the data by creating new features or combining existing ones, making the data more interpretable and predictive;
- data analysis algorithms which deeply analyze and mine the processed data to find trends and correlations in the data and obtain analysis results;
- here, the data analysis algorithms comprise statistical analysis, machine learning algorithms, deep learning algorithm, and more; specifically, the data analysis algorithms typically involve the following key tasks:
- the statistical analysis serves as the foundation of data analysis, and by calculating various statistical metrics of the data such as mean, variance, and correlation coefficients, the basic features and distribution of the data are described; the statistical analysis helps to understand the centralized tendency and dispersion degree of the data, as well as correlations among different variables, thereby revealing the overall characteristics of the data;
- the machine learning algorithms are a class of algorithms that can learn from data and extract patterns and rules; through learning and training on large volumes of historical data, the machine learning algorithms can discover hidden patterns in the data and establish prediction models to predict future trends and states; examples of the machine learning algorithms applicable in this embodiment include linear regression, decision trees, support vector machines, and random forests;
- the deep learning algorithm is a type of machine learning method based on artificial neural networks, which learns complex features and representations of data through multi-layer neural network structures; the deep learning algorithm excels in handling large-scale data and complex pattern recognition tasks, automatically learning abstract representations from the data and applying the same to prediction, classification, clustering, and other tasks; and
- a prediction model which is established according to the analysis results and used for predicting a future usage status of the respiratory protection device.

The prediction model may be established using various machine learning algorithms or statistical models, such as linear regression, decision trees, random forests, and neural networks. These models convert the features and correlations obtained from data analysis into patterns and rules that can be used for prediction, allowing for accurate prediction of future device statuses. The establishment of prediction models requires training and validation to ensure they possess good generalization ability and prediction accuracy, meeting the needs of practical applications.

The data analysis algorithms provide the foundation and support for the prediction models, helping to identify patterns and correlations within the data. The prediction models, in turn, are established based on analysis results to predict future trends and statuses. By integrating the two processes, a more comprehensive understanding and utilization of the data can be achieved, thereby enhancing the accuracy and reliability of prediction.

Here, the prediction model is an LSTM model, comprising:
- an input layer for receiving the analysis results;
- an LSTM layer for learning the long-term dependence of time series data in the analysis results and generating an internal representation;
- an output layer for receiving the internal representation from the LSMT layer and generating final prediction results; and
- a sliding window which divides the time series data from the analysis results into different windows and allows for movement on a time axis in a sliding manner to generate a series of subsequence data and input the same into the LSTM layer.

Using deep learning models such as LSTM for prediction can better capture long-term dependencies and complex patterns in time series data, thereby enhancing the accuracy and stability of prediction. When combined with sliding window techniques, this approach can increase the diversity and richness of the data, improving the generalization ability and predictive performance of the model.

Taking the following specific situation as an example, assume we need to predict the lifespan of the filter component in the respiratory protection device:

First, a series of data regarding the usage status of the filter component is collected from the respiratory protection device, which may include information such as working hours, working temperature, and working humidity. Then, the data undergoes processing and analysis, including data cleaning, conversion, and normalization, resulting in a set of analysis results for prediction.

Next, the analysis results are input into the prediction model. In the input layer, the analysis results are passed to the LSTM layer, which learns the time series patterns and long-term dependencies present in the data, such as how the usage pattern of the filter component changes over time. By learning these patterns, the LSTM layer generates internal representations that capture the underlying rules and trends within the data. In the output layer, the internal representations from the LSTM layer are received and transformed into the final prediction result, which is the lifespan prediction of the filter component. The prediction result may indicate when the filter component may need to be replaced in the future, allowing for proactive maintenance measures to be taken and preventing device downtime or performance issues due to filter component failure.

Additionally, by introducing the sliding window method, the original time series data can be divided into different windows that slide along the time axis, generating a series of subsequence data. The advantage of this approach is that it increases the diversity and richness of the data, thereby enhancing the generalization ability and prediction accuracy of the model.

The aforementioned model structure is suitable for processing various types of component data, including but not limited to filter components, battery components, and sensor components. Regardless of the type of component data, prediction models can be employed for analysis and prediction to effectively manage and maintain the usage status of each component in the respiratory protection device. In the specific application scenarios of the respiratory protection device, certain component data exhibit distinct temporal characteristics. For example, the lifespan of the filter component changes over time, the capacity and performance of batteries may gradually decline as the number of charge-discharge cycles increases, and the sensor component may be affected by environmental factors over extended use, resulting in performance degradation or failure. The LSTM model can capture long-term dependencies and patterns in such time series data, enabling accurate prediction of component usage statuses. Moreover, the sliding window technique enhances the diversity and richness of the data, better reflecting the temporal characteristics of the data and improving the generalization ability and predictive performance of the model.

In the implementation process, the sliding method of the sliding window may be achieved by setting two key parameters:

Window Size: This denotes the number of time series data points contained in each window. The window size typically needs to be determined based on the characteristics of the data and the prediction task, and can be fine-tuned based on experience or experimentation.

Sliding Step: This indicates the distance the sliding window moves along the time axis during each slide, also known as sliding interval. It is used to control the degree of overlap and continuity between windows. A smaller sliding step can increase the overlap between windows, thereby enhancing data utilization and model stability, but it also increases computational load. Conversely, a larger sliding step can reduce overlap, decrease computational load, but may result in some loss of information.

Preferably, the relationship between the window size and the sliding step may be optimally defined as follows:

$$S = W \times (\alpha + \beta)/2$$

where S represents the sliding step, W represents the window size, $\alpha$ and $\beta$ denote a periodic factor and a trend factor respectively, which are adjusted based on the trends identified in the analysis results of the data analysis algorithms; the unit of S depends on the unit of W, with W generally measured in time units, such as days and hours, and $\alpha$ and $\beta$ are pure numerical values without units, ranging from 0 to 1, representing the degree of influence of the corresponding factors on the sliding step.

Specifically, the periodic factor $\alpha$ takes into account periodic variations in the data, such as seasonal changes or the impact of cyclical events on the usage status of the respiratory protection device. A common method for calculating the periodic factor involves using Fourier transforms or autocorrelation functions to analyze the periodic features of the data and extract the value of the periodic factor. The specific calculation may involve complex frequency domain analysis techniques to identify periodic components in the data and quantify their impact. The trend factor $\beta$ takes into account trend variations in the data, such as a sustained increase or decrease over time. Methods for calculating the trend factor may be based on linear regression, moving averages, or other time series analysis techniques to determine the overall trend direction and rate of change of the data. The specific calculation may involve fitting the data or estimating trend lines to obtain the value of the trend factor.

Overall, both the periodic factor $\alpha$ and the trend factor $\beta$ are adjusted to better reflect the characteristics of the data, but they focus on periodic and trend changes in the data respectively, thus playing different roles when adjusting the sliding window.

In the specific context of the respiratory protection device, the technical advantages of adopting the above scheme are reflected in the following aspects.

More Accurate Prediction: By adjusting the periodic factor $\alpha$ and the trend factor $\beta$, the size and step of the sliding window can better adapt to the periodic and trend changes in the usage status of the respiratory protection device. For instance, if the device experiences seasonal variations or long-term trends, adjusting the two factors allows the sliding window to more effectively capture the features, thereby improving prediction accuracy.

More Effective Data Utilization: By optimizing the sliding window technique, it is possible to increase the continuity between windows while maintaining a certain degree of overlap, thus enhancing data utilization. In the context of the respiratory protection device, if data from a specific time period significantly impacts the prediction of the status of the device in the next period, an appropriately designed sliding window can make full use of the information, allowing the model to more accurately capture changes in device status.

Reduced Information Loss: By adjusting the sliding step, it is possible to reduce computational load while maintaining prediction accuracy. A smaller sliding step increases the overlap between windows, enhancing data continuity and reducing information loss; on the other hand, a larger sliding step can reduce computational load, improving the efficiency of model training and prediction. In the prediction tasks for the respiratory protection device, this means that large volumes of time series data can be processed more efficiently while ensuring prediction accuracy.

Embodiment II

A communication method for a respiratory protection device, which adopts the communication system for a respiratory protection device as described in Embodiment I, comprises:
    collecting pairing information of two components installed on the respiratory protection device and requiring relative installation, and collecting component information of at least one of the components;
    transmitting the pairing information and the component information through communication connection;
    processing the transmitted pairing information and component information; and
    storing different processing results of the pairing information and component information in a centralized manner.
The technical effects of this embodiment are as described in Embodiment I, which will not be repeated here.

Embodiment III

A respiratory protection system comprises a plurality of respiratory protection devices and the communication system for a respiratory protection device as described in Embodiment I;
    the communication system comprises a plurality of pairing transmission modules which are respectively installed on two different components requiring relative installation on the plurality of respiratory protection devices;
    the communication system collects, processes and stores the identity information and pairing information of different respiratory protection devices in a centralized manner through the main control module and the plurality of pairing transmission modules; and
    the main control module is connected with a fan of the respiratory protection device, at least controls the supplied airflow of the fan according to processing results, and monitors a usage status of the specified component.

In the implementation process, compared to the technical effects achievable in Embodiment I, this embodiment can further enable more precise control of the respiratory protection device. For instance, through the control of airflow supplied by the main unit, airflow adjustments can be made for different filter components to meet specified noise requirements. Specifically, when the filter component adopts a filter canister, the airflow must be reduced due to its high resistance, while a standard filter cartridge, which has lower resistance, allows for an increase in airflow. By controlling the supplied airflow of the fan through the main control module, airflow adjustments can be made based on the characteristics of different filter components to satisfy the set noise requirements. This level of precise control ensures the performance and comfort of the respiratory protection device under varying operating conditions.

Monitoring the usage status can be effectively achieved through component information, which includes detailed data about each component, such as production date, materials, versions, and more. This also encompasses usage time for filter cartridges and filter canisters, as well as the remaining battery power of battery packs. This information aids in real-time monitoring of the operational status of the device, allowing for timely detection of issues and corresponding measures, thereby enhancing the reliability and safety of the device. Additionally, the main control module enables remote control of the respiratory protection device, allowing operators to adjust the operating parameters of the device from a distance and conduct remote maintenance and management. This functionality increases the level of intelligence and convenience in using the device.

The respiratory protection system in this embodiment enhances the monitoring, control, and management capabilities for respiratory protection devices through further technical improvements and functional enhancements, providing users with a safer, more convenient, and comfortable using experience. In specific implementation, a display apparatus can be installed, with display functionality being implemented via screens such as LCD screens, segmented displays, and touch screens. The displayed content may encompass one or several of the following functions: the connection status of components, including filter cartridges, filter canisters, hoses, etc.; usage time; degree of aging; the usage status of a respirator; various alarm notifications, including warnings for uninstalled filter cartridges, blockages, uninstalled filter canisters, excessive usage time, fan abnormalities, motherboard issues, battery pack anomalies, and others.

The basic principles, main features and advantages of the invention are described above. Those skilled in the art should understand that the invention is not limited by the above-mentioned embodiments. What is described in the above-mentioned embodiments and the description is only to illustrate the principles of the invention. Without departing from the spirit and scope of the invention, the invention will have various changes and improvements, which all fall within the scope of the claimed invention. The protection scope of the invention is defined by the appended claims and their equivalents.

What is claimed is:

1. A communication system for a respiratory protection device, comprising:
    pairing transmission modules, each comprising a first pairing unit and a second pairing unit which are paired and connected within a specified location area and are respectively installed on different components of the respiratory protection device; and
    a main control module connected with the plurality of pairing transmission modules and comprising a communication unit, a control unit and a storage unit; wherein
    the communication unit is in communication connection with the pairing transmission modules for information transmission;
    the control unit collects and processes identity information of the first pairing unit and/or the second pairing unit and pairing information of the first pairing unit and the second pairing unit, the identity information at least comprising component information of the respiratory protection device;
    the storage unit stores collection and processing results of the identity information and the pairing information;
    the main control module also comprises a data processing unit which processes and analyzes data stored in the storage unit and predicts a usage status of the respiratory protection device according to analysis results;

the data processing unit comprises:
a data processor for processing the data obtained from the storage unit, the processing at least comprising data cleaning, conversion, normalization and feature engineering;
data analysis algorithms which deeply analyze and mine the processed data to find trends and correlations in the data and obtain analysis results; and
a prediction model which is established according to the analysis results and used for predicting a future usage status of the respiratory protection device;
the prediction model is an LSTM model, comprising:
an input layer for receiving the analysis results;
an LSTM layer for learning the long-term dependence of time series data in the analysis results and generating an internal representation;
an output layer for receiving the internal representation from the LSMT layer and generating final prediction results; and
a sliding window which divides the time series data from the analysis results into different windows and allows for movement on a time axis in a sliding manner to generate a series of subsequence data and input the same into the LSTM layer; and
the relationship between a window size and a sliding step is defined as follows:

$$S=W\times(\alpha+\beta)/2$$

where S represents the sliding step, W represents the window size, $\alpha$ and $\beta$ denote a periodic factor and a trend factor respectively, which are adjusted based on the trends identified in the analysis results of the data analysis algorithms; the unit of S depends on the unit of W, with W measured in time units, and $\alpha$ and $\beta$ are pure numerical values without units, ranging from 0 to 1, representing the degree of influence of the corresponding factors on the sliding step; and the periodic factor $\alpha$ takes into account periodic variations in the data, and the trend factor $\beta$ takes into account trend variations in the data.

2. The communication system for a respiratory protection device according to claim 1, further comprising a positioning module installed at a specified location of the respiratory protection device; wherein
the communication unit is in communication connection with the positioning module;
the control unit collects and processes positioning information of the positioning module; and
the storage unit stores collection and/or processing results of the positioning information.

3. The communication system for a respiratory protection device according to claim 1, wherein the collection and processing of the identity information by the control unit comprises:
continuously assessing whether a new pairing transmission module is successfully paired until the assessment result is yes, and collecting the identity information of the first pairing unit and/or the second pairing unit in the pairing transmission module; and
endowing the identity information with:
a unique identifier part which records unique identifier of specified components on the respiratory protection device where the first pairing unit and/or the second pairing unit are installed; and
a dynamic identifier part which records real-time setting parameters of the specified components.

4. The communication system for a respiratory protection device according to claim 3, wherein the storage unit stores the unique identifier part only once through a first storage area, and stores the dynamic identifier part corresponding to the unique identifier part through a second storage area.

5. The communication system for a respiratory protection device according to claim 4, wherein establishing a correspondence between the first storage area and the second storage area comprises:
establishing a virtual file system in the first storage area, and mapping each unique identifier to a unique file path or file name; and
storing dynamic data of the real-time setting parameters in the second storage area in the form of files, paths or file names of each file corresponding to the unique identifiers.

6. A communication method for a respiratory protection device, which adopts the communication system for a respiratory protection device according to claim 1, comprising:
collecting pairing information of two components installed on the respiratory protection device and requiring relative installation, and collecting component information of at least one of the components;
transmitting the pairing information and the component information through communication connection;
processing the transmitted pairing information and component information; and
storing different processing results of the pairing information and component information in a centralized manner.

7. A respiratory protection system, comprising a plurality of respiratory protection devices and the communication system for a respiratory protection device according to claim 1, wherein
the communication system comprises a plurality of pairing transmission modules which are respectively installed on two different components requiring relative installation on the plurality of respiratory protection devices;
the communication system collects, processes and stores the identity information and pairing information of different respiratory protection devices in a centralized manner through the main control module and the plurality of pairing transmission modules; and
the main control module is connected with a fan of the respiratory protection device, at least controls the supplied airflow of the fan according to processing results, and monitors a usage status of the specified component.

* * * * *